(12) United States Patent
Kim et al.

(10) Patent No.: US 11,912,629 B2
(45) Date of Patent: Feb. 27, 2024

(54) METHOD FOR ENHANCING MECHANICAL PROPERTIES IN SINTERED CERAMIC BODIES HAVING APPLICATIONS IN DENTAL RESTORATIONS

(71) Applicant: James R. Glidewell Dental Ceramics, Inc., Newport Beach, CA (US)

(72) Inventors: Jae Won Kim, Irvine, CA (US); Enoch Park, Corona, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 136 days.

(21) Appl. No.: 17/474,407

(22) Filed: Sep. 14, 2021

(65) Prior Publication Data

US 2022/0081369 A1     Mar. 17, 2022

Related U.S. Application Data

(60) Provisional application No. 63/077,935, filed on Sep. 14, 2020.

(51) Int. Cl.
| | | |
|---|---|---|
| C04B 41/00 | (2006.01) | |
| A61K 6/20 | (2020.01) | |
| (Continued) | | |

(52) U.S. Cl.
CPC ............. C04B 41/009 (2013.01); A61K 6/20 (2020.01); A61K 6/818 (2020.01); C04B 35/48 (2013.01);
(Continued)

(58) Field of Classification Search
CPC ........ C04B 41/009; C04B 35/486; A61K 6/20
See application file for complete search history.

(56) References Cited

U.S. PATENT DOCUMENTS 6,380,113 B1   4/2002   Kim et al.
8,298,329 B2 *   10/2012   Knapp ................ C04B 35/486
                                                      106/35
(Continued)

FOREIGN PATENT DOCUMENTS

EP          2889279 A1    7/2015
KR     20170046212 A    5/2017

OTHER PUBLICATIONS

E. Camposilvan, et al., Mechanical properties of alumina infiltrated zirconia nanocomposites XIII Congreso Nacional de Propiedades Mecánicas de Solidos, PMS2012 (Alcoy-Alicante), pp. 203-208.
(Continued)

*Primary Examiner* — Dah-Wei D. Yuan
*Assistant Examiner* — Andrew J Bowman
(74) *Attorney, Agent, or Firm* — Charles Fowler

(57) ABSTRACT

A method for enhancing mechanical properties of sintered, zirconia ceramic bodies and zirconia ceramic dental restorations is provided. A porous or pre-sintered stage of a ceramic body may be treated with a tantalum-containing composition prior to sintering. Alternatively, zirconia ceramic powder may be coated with a tantalum-containing composition prior to forming a shaped ceramic body. After sintering, the resulting ceramic bodies have enhanced mechanical properties, such as greater fracture toughness, without a significant decrease in optical properties.

18 Claims, 14 Drawing Sheets

(51) Int. Cl.
- *A61K 6/818* (2020.01)
- *C04B 35/48* (2006.01)
- *C04B 35/64* (2006.01)
- *C04B 41/45* (2006.01)
- *C04B 41/50* (2006.01)

(52) U.S. Cl.
CPC .......... *C04B 35/64* (2013.01); *C04B 41/4535* (2013.01); *C04B 41/5027* (2013.01); *C04B 2235/3246* (2013.01); *C04B 2235/3251* (2013.01); *C04B 2235/96* (2013.01)

(56) References Cited

U.S. PATENT DOCUMENTS

| | | |
|---|---|---|
| 8,815,327 B2 | 8/2014 | Zhang et al. |
| 9,095,403 B2 | 8/2015 | Carden et al. |
| 9,365,459 B2 | 6/2016 | Carden et al. |
| 9,434,651 B2 | 9/2016 | Carden |
| D769,449 S | 10/2016 | Leeson et al. |
| 9,512,317 B2 | 12/2016 | Carden |
| 9,545,363 B2 | 1/2017 | Kim et al. |
| D781,428 S | 3/2017 | Leeson et al. |
| 9,597,265 B2 | 3/2017 | Carden et al. |
| 10,479,729 B2 | 11/2019 | Valenti et al. |
| 10,532,008 B2 | 1/2020 | Balasubramanian et al. |
| 2009/0118114 A1 | 5/2009 | Zhang et al. |
| 2015/0183690 A1 | 7/2015 | Kim et al. |
| 2016/0368826 A1 | 12/2016 | Calado Da Silva et al. |

OTHER PUBLICATIONS

G.P. Cammarota, et al., Effect of Ni, Si and Cr in the structural formation of diffusion aluminide coatings on commercial-purity titanium, Institute of Metallurgy, Bologna, Italy, Elsevier, Science Direct, Surface & Coatings Technology 201 (2006) pp. 230-242.

G.M. Kim, et al., Platinum-Modified Diffusion Aluminide Coatings on Nickel-Base Superalloys, Army Research Laboratory, prepared by Material Science and Engineering Department, University of Pittsburgh, under contract DAAG46-85-K-0008, In 33 pages.

Sung R. Choi, et al., Strength, Fracture Toughness, and Slow Crack Growth of Zirconia / Alumina Composite at Elevated Temperature, NASA/TM-2003-212108, Feb. 2003, National Aeronautics and Space Administration, Glenn Research Center, in 18 pages.

\* cited by examiner

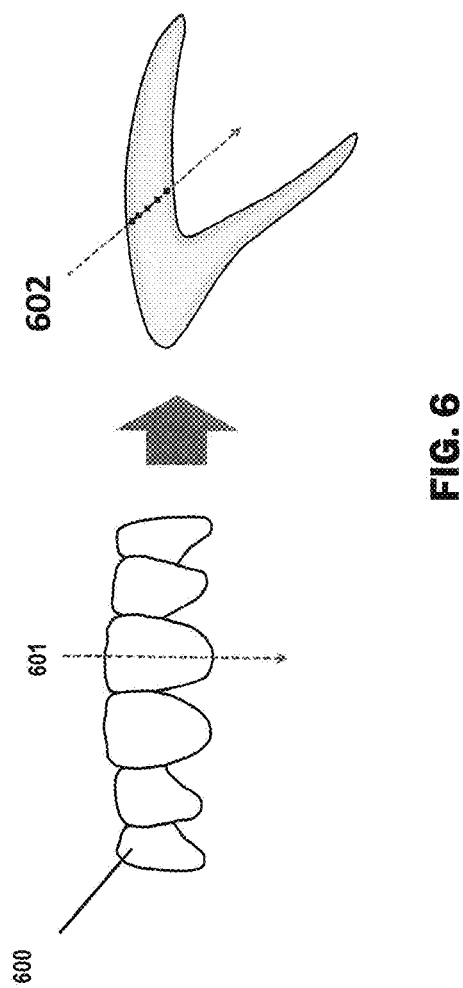

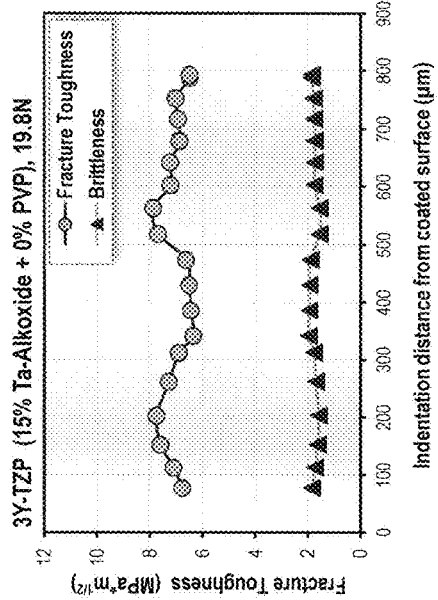
FIG. 7A
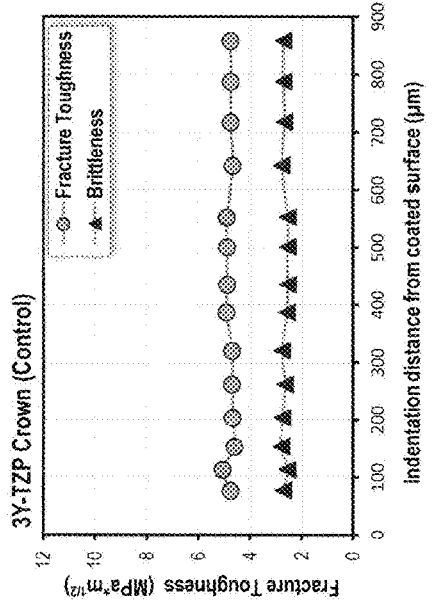
FIG. 7C
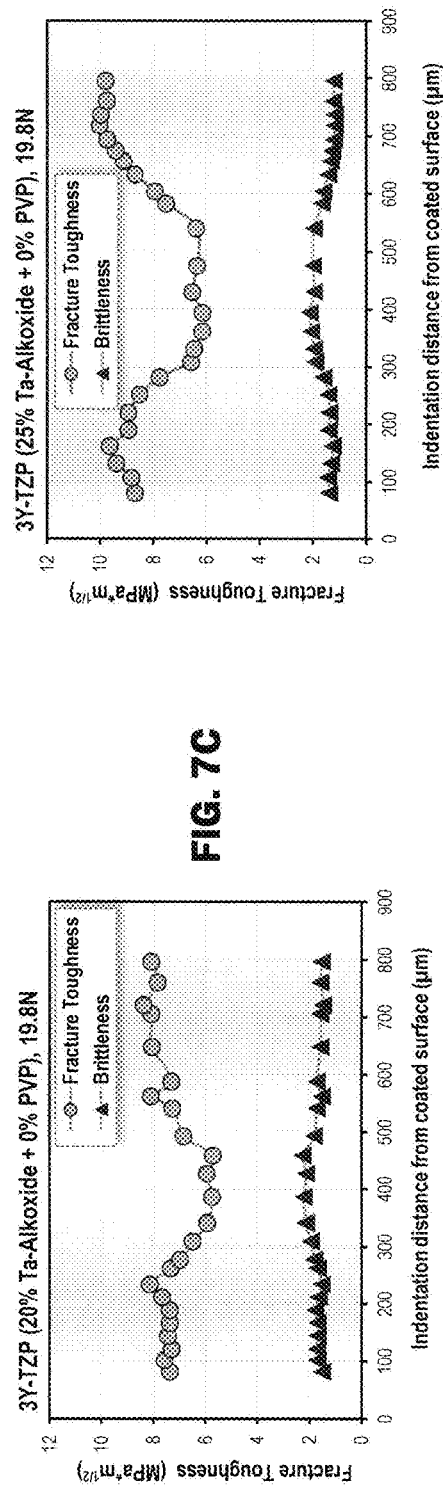
FIG. 7B
FIG. 7D

| Material | SAMPLE | TANTALUM ALKOXIDE% | PVP% | 3-Point Flexural Strength (MPa) | Stdev | Shape | Characteristic (MPa) | Surface Fracture Toughness (MPa·m$^{½}$) | Stdev |
|---|---|---|---|---|---|---|---|---|---|
| 3Y-TZP | Control | 0% | 0% | 959 | 138.69 | 6.4 | 1027 | 5.4 | 0.2 |
| | 13A | 15% | 0% | 1040 | 71 | 14.2 | 1075 | 8.4 | 0.1 |
| | 13B | 15% | 2.50% | 1009 | 116 | 8.5 | 1064 | 8.3 | 0.2 |
| | 13C | 15% | 5% | 1024 | 88 | 11.4 | 1066 | 8.6 | 0.1 |
| | 13D | 20% | 0% | 905 | 51 | 17.5 | 929 | 9.3 | 0.2 |
| | 13E | 25% | 0% | 841 | 20 | 41 | 851 | 11.3 | 0.1 |
| | 13F | 30% | 0% | 838 | 59 | 12.1 | 871 | 10.4 | 0.1 |

FIG. 13

| Material | SAMPLE | TANTALUM ALKOXIDE% | PVP% | 3-Point Flexural Strength (MPa) | Stdev | Shape | Characteristic (MPa) | Surface Fracture Toughness (MPa·m^½) | Stdev |
|---|---|---|---|---|---|---|---|---|---|
| 4Y-PSZ | 14Control | 0% | 0% | 920 | 126.82 | 6.1 | 989 | 3.8 | 0.3 |
| | 14A | 30% | 0% | 1002 | 103 | 9 | 1053 | 7.3 | 0.1 |
| | 14B | 30% | 2.50% | 1004 | 164 | 5.7 | 1082 | 10.3 | 0.2 |
| | 14C | 30% | 5% | 918 | 170 | 5.2 | 993 | 9.2 | 0.1 |
| | 14D | 35% | 0% | 955 | 83.44 | 10.8 | 997 | 10.9 | 0.2 |
| | 14E | 40% | 0% | 883 | 51.28 | 15.9 | 909 | 6.0 | 0.1 |
| | 14F | 45% | 0% | 890 | 67.42 | 11.6 | 926 | 9.9 | 0.1 |

FIG. 14

| Material | SAMPLE | TANTALUM ALKOXIDE% | PVP% | 3-Point Flexural Strength (MPa) | Stdev | Shape | Characteristic (MPa) | Surface Fracture Toughness (MPa·m^(½)) | Stdev |
|---|---|---|---|---|---|---|---|---|---|
| 5Y-PSZ | 15Control | 0% | 0% | 595 | 63.81 | 11.96 | 618 | 2.6 | 0.2 |
| | 15A | 45% | 0% | 1088 | 131 | 5.9 | 1174 | 10.6 | 0.1 |
| | 15B | 45% | 2.50% | 1142 | 67 | 16.4 | 1175 | 10.8 | 0.2 |
| | 15C | 45% | 5% | 1003 | 183 | 4.3 | 1105 | 11.0 | 0.1 |
| | 15D | 50% | 0% | 1092 | 127 | 8.4 | 1153 | 11.1 | 0.2 |
| | 15E | 55% | 0% | 1203 | 155 | 6.6 | 1286 | 11.2 | 0.1 |
| | 15F | 60% | 0% | 1096 | 170 | 4.1 | 1220 | 11.0 | 0.1 |

FIG. 15

METHOD FOR ENHANCING MECHANICAL PROPERTIES IN SINTERED CERAMIC BODIES HAVING APPLICATIONS IN DENTAL RESTORATIONS

RELATED APPLICATIONS

This application claims the benefit of, and priority to, U.S. Provisional Patent Application No. 63/077,935, filed Sep. 14, 2020. The entirety of the foregoing application is incorporated herein by reference.

BACKGROUND

Prosthetic dentistry is undergoing a transition from ceramo-metal to all ceramic fabrication, both for the esthetic benefits to patients and the manufacturing advantages of precision-milled monolithic construction. The most popular dental ceramic systems are silica, lithium disilicate, leucite, alumina, and zirconia-based materials. Currently, among all dental ceramics, zirconia. ($ZrO_2$) is the material of choice in contemporary restorative dentistry because of its superior mechanical properties, translucency, color stability, and biocompatibility. It has high-temperature stability and melting point (2680° C.), high flexural strength in the range of 900-1200 MPa, compression strength of ~2000 MPa, a high thermal expansion coefficient ($>10\times10^{-6}$ $K^{-1}$), low thermal conductivity ($<1$ W $m^{-1}$ $K^{-1}$) and high thermal shock resistance ($\Delta T=400\text{-}500°$ C.).

Dental zirconia, usually used for restorations, is a modified yttria ($Y_2O_3$) tetragonal zirconia polycrystal (Y-TZP). The TZP that is stabilized with 3 mol percent yttria, known as 3Y-TZP, is commonly used for many dental applications because of its superior mechanical properties, low porosity, and high density. For example, BruxZir® Full-Strength (Glidewell Laboratories) is a 3Y-TZP that has been used for over ten years and millions of dental restorations.

The 3Y-TZP has a fracture toughness of 4.5 to 5 MPa·$m^{1/2}$ and flexural strength of 950-1050 MPa (3 point bend test strength). However, this exceptionally strong 3Y-TZP has reduced translucency, which reduces its application in esthetically demanding clinical situations. The translucency is improved by increasing the cubic (c) phase content of the bulk material. This can be achieved by using (or increasing the concentration of) stabilizers such as yttria, magnesia, or a number of lanthanides, e.g., providing higher yttria content of 4-mole percentage (4Y-TZP) to 5-mole percentage (5YTZP) or higher. The light transmission is increased by 43% to 45% due to increased c-phase. However, the c-phase diminishes the stress-induced transformation toughening effect of tetragonal zirconia, resulting in reduced strength and toughness. The flexural strength of 5Y-TZP is in the range of 600-800 MPa and fracture toughness of 2.2 to 4 MPa·$m^{1/2}$. Hence, 5Y-TZP materials, while showing significantly increased esthetics, are restricted to single unit and short span dental prostheses in the anterior zone. Therefore, to capitalize on the esthetic advantages of increased translucency, it would be beneficial to increase the strength of these 5Y-TZP materials.

SUMMARY

A method and chemical compositions for enhancing mechanical properties in sintered zirconia ceramic bodies are provided. Sintered, yttria-stabilized zirconia ceramic bodies treated with a tantalum-containing or niobium-containing composition prior to sintering exhibit enhanced mechanical properties, such as flexural strength, fracture toughness, and the like, in the sintered bodies. The sintered zirconia ceramic bodies are suitable for use as dental restorations, such as an implant, implant abutment, crown, veneer, partial or full-arch denture, implant-supported denture and bridge. Enhanced properties may be substantially permanent for the useful life of the restoration. Tantalum-containing solutions and niobium-containing solutions described herein may have a stable shelf-life under ambient conditions for at least six months, such as up to two years or more.

A method is provided that comprises treating a porous, yttria-stabilized zirconia ceramic body with a tantalum (or niobium) containing composition, penetrating at least a portion of the porous zirconia body with the composition, and sintering the ceramic body to at least 98% of theoretical density. Tantalum (or niobium) containing compositions may be applied to the entire outer surface of a ceramic body, or to selective regions of a dental restoration that are prone to cracking or chipping. For example, the tantalum (or niobium) containing composition may be applied to the margin of a crown where the ceramic material tapers near the gingival contact area and is susceptible to chipping. Alternatively, a tantalum (or niobium) containing composition may be applied at an attachment point or through hole of a ceramic denture to prevent cracking or fracture. In other embodiments, a tantalum (or niobium) containing solution may be applied to the entire outer surface of a zirconia ceramic implant to enhance flexural strength.

Tantalum (or niobium) containing compositions are provided that comprise a tantalum (or niobium) containing material and optionally, a polymer, in one or more solvents. For example, in an embodiment, a tantalum-containing composition comprises 10-70 wt % of a tantalum-containing chloride or alkoxide, 25-90 wt % of a solvent comprising ethanol, isopropanol, butanol, pentanol, or a combination thereof, 0-5 wt % of methanol, 0-5 wt % of a polyvinyl pyrrolidone, and 0-2 wt % rhodamine B as a coloring agent.

Optionally, a sandblasting treatment may be applied to a portion of the ceramic body treated that has been with the tantalum (or niobium) containing composition. Regions of a ceramic body treated with a tantalum (or niobium) containing composition and a sandblasting treatment demonstrate further enhancements of flexural strength, fracture toughness or both.

Translucencies of yttrium-stabilized zirconia ceramic bodies treated with tantalum (or niobium) containing solution are substantially the same as untreated ceramic bodies of the same ceramic material. Sintered restorations made by the methods described herein have a color space (CIE L*a*b*) values within a desired range for use in anterior and/or posterior dental restoration applications. Thus, methods and compositions are described for forming sintered ceramic dental restorations in selected shades that have enhanced translucency and suitable strength.

BRIEF DESCRIPTION OF THE FIGURES

FIG. 6 is a schematic diagram showing an example dental restoration and a method for performing a micro indentation test.

FIGS. 7A-7D, 8A-8C, 9A-9C, and 10A-10C are graphs showing fracture toughness and brittleness values for sample restorations (crowns) at locations having selected distances from the coated surface of the restorations (crowns).

FIG. 129 is a graph illustrating critical load (N) values for an untreated 3-unit bridge dental restoration and a treated 3-unit bridge dental restoration obtained using the method illustrated in FIG. 12A.

FIGS. 13-15 are tables containing results of tests of 3-point flexural strength and surface fracture toughness of untreated zirconia samples and zirconia samples that have been treated with the tantalum containing compositions described herein.

DETAILED DESCRIPTION

A method is provided for treating an yttria-stabilized zirconia ceramic body by applying a tantalum (or niobium) containing composition to the ceramic body in the pre-sintered or bisque stage. Tantalum (or niobium) containing compositions may be applied to green (unsintered) ceramic bodies, or pre-sintered ceramic bodies that retain at least partial porosity for penetration of the tantalum (or niobium) containing composition into the thickness of the material form.

Figure 1A:
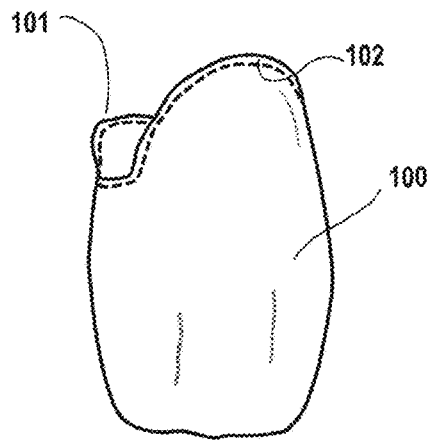
FIGS. 1A, 1B, 1C, and 1D are perspective views of dental restorations.
Figure 1B:
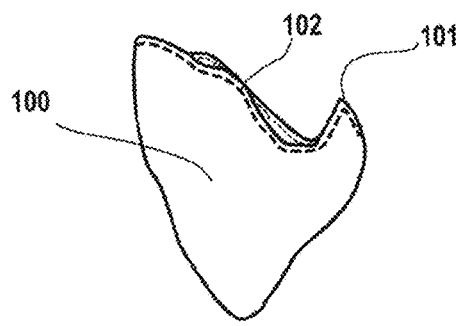
Figure 1C:
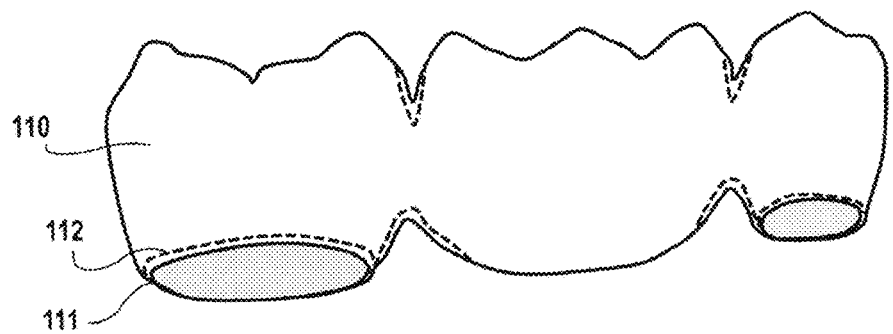
Figure 1D:
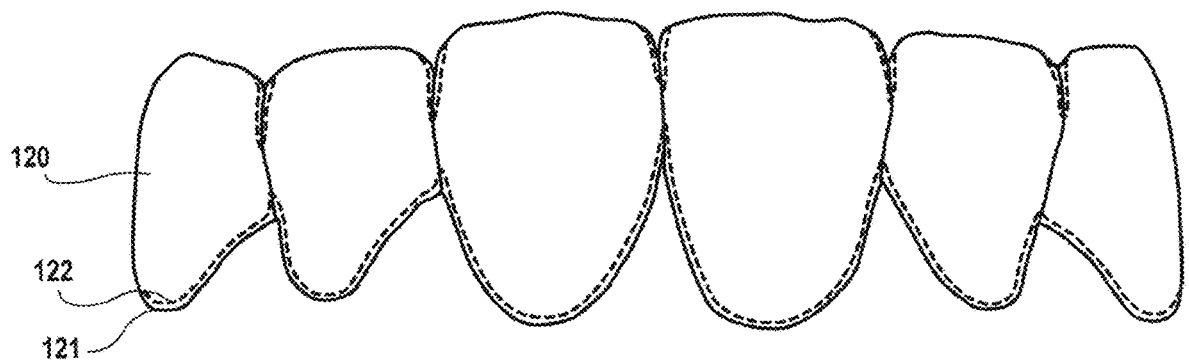

In one embodiment, with reference to FIGS. 1A and 1B, a bisque stage ceramic crown 100 is treated by brush coating a liquid tantalum-containing composition on the margin 101 where the thickness of the ceramic material tapers to the edge. The tantalum-containing composition may be applied to a surrounding margin region 102 for a distance sufficient to provide a region having increased flexural strength and fracture toughness without significantly decreasing the optical properties of the material. In another embodiment, with reference to FIG. 1C, a bisque stage three-unit bridge 110 is treated by brush coating a liquid tantalum-containing composition on the margin 111 where the thickness of the ceramic material tapers to the edge. The tantalum-containing composition may be applied to a surrounding margin region 112 for a distance sufficient to provide a region having increased flexural strength and fracture toughness without significantly decreasing the optical properties of the material. In still another embodiment, with reference to FIG. 1D, a plurality of bisque stage veneers 120 are treated by brush coating a liquid tantalum-containing composition on the margins 121 where the thickness of the ceramic material tapers to the edge. The tantalum-containing composition may be applied to a surrounding margin region 122 for a distance sufficient to provide a region having increased flexural strength and fracture toughness without significantly decreasing the optical properties of the material.

Liquid tantalum (or niobium) containing compositions comprise an amount of tantalum (or niobium) in a sufficient amount to achieve a selected enhancement of mechanical properties in a sintered ceramic body. A liquid component may be selected in which the desired amount of tantalum (or niobium) containing material remains in solution. The liquid may comprise water, or an organic solvent such as, methanol, ethanol, isopropanol, butanol, pentanol, butyraldehyde, acetone, or combinations thereof. In some embodiments, the solvent is less than 99% pure. In other embodiments, a solvent having an impurity or water content that is less than 4 wt % (e.g., anhydrous ethanol), two or more solvents may be used in combination. In one embodiment, a liquid tantalum-containing composition comprises a mixture of methanol and isopropanol. In another embodiment, a liquid tantalum-containing composition comprises a mixture of butyraldehyde and acetone.

The tantalum (or niobium) containing material may comprise an oxide or salt containing tantalum (or niobium), such as, tantalum (or niobium) chloride or tantalum (or niobium) alkoxide. The amount of tantalum-containing material in a tantalum-containing composition may range from approximately 10% by weight (wt %) to approximately 70 wt % of the tantalum-containing composition. In some embodiments, a tantalum-containing composition comprises from 10 wt % to 40 wt. % of the tantalum-containing material, based on the total weight of the tantalum-containing composition, or from 40 wt. % to 70 wt. %, or from 45 wt. % to 70 wt. %, or from 45 wt. % to 65 wt. %, or from 50 wt. % to 70 wt. %, or from 55 wt. % to 65 wt. %, of the tantalum-containing material, based on the total weight of the tantalum-containing composition. Examples of tantalum-containing materials include, but are not limited to, tantalum chloride (e.g., tantalum (V) chloride anhydrous), and tantalum alkoxide (e.g., tantalum (V) methoxide, tantalum (V) isopropoxide or tantalum (V) ethoxide).

In one specific embodiment, a tantalum-containing solution comprises 10 wt % to 40 wt % of tantalum chloride hexahydrate and from 60 wt % to 90 wt % isopropanol.

In another embodiment, a tantalum-containing solution comprises from 10 wt % to 60 wt % tantalum ethoxide and 35 wt % to 90 wt % isopropanol, and 0 wt % to 5 wt % of an organic additive, e.g., polyvinylpyrrolidone (PVP).

In a further embodiment, a tantalum-containing solution comprises from 10 wt % to 60 wt % tantalum ethoxide and 35 wt % to 89 wt % isopropanol, 1 wt % to 10 wt % methanol, and 0 wt % to 5 wt % of polyvinylpyrrolidone (PVP).

In a further embodiment, a tantalum-containing solution comprises from 30 wt % to 60 wt % tantalum ethoxide and 40 wt % to 70 wt % ethanol. In a further embodiment, an equivalent amount of ethanol (by weight percent) may be replaced with 1 wt % to 10 wt %, or from 1 wt % to 5 wt %, of polyvinylpyrrolidone (PVP).

In another embodiment, a tantalum-containing solution comprises from 30 wt % to 60 wt % tantalum ethoxide and 40 wt % to 70 wt % acetone and butyraldehyde mixture.

A color marker may be added to the tantalum (or niobium) containing composition, such as an organic colorant that burns off upon sintering, such as rhodamine B. Rhodamine B may be present in an amount sufficient to facilitate application of the composition to the ceramic body.

A wetting agent may be added to control the depth of penetration of the tantalum (or niobium) containing composition into the porous ceramic body. Wetting agents include, but are not limited to polymers that are soluble in the solvent system of the composition.

In one embodiment, a tantalum-containing composition comprises 10 wt % to 70 wt % tantalum-containing material, 35 wt % to 90 wt % of a solvent comprising methanol, ethanol, isopropanol or a combination thereof, wherein the solvent comprises less than 3 wt % water, and optionally, a polymer. In some embodiments, where the solvent comprises less than 49 wt % anhydrous IPA and less than 40 wt % anhydrous ethanol, the tantalum-containing composition is stable for at least 6 months at ambient conditions.

A coloring agent may also be added to the tantalum (or niobium) containing composition in an amount to achieve a specific lightness, hue and/or chroma value in the final sintered ceramic body. One or more metallic compounds or metallic complexes may be selected to impart a shade suitable for use in dental restorations, such as a shade based on an industry-recognized shade guide, such as the VITA Classical® Shade Guide. Metallic compounds and metallic complexes may contain transition metals from groups 3 through 14 on the periodic table, rare earth metals, and mixtures thereof. Metal-containing components in the form of metal oxides, alkoxides or metal salts may contain anions, including but not limited to, $OH^-$, $Cl^-$, $SO_4^{2-}$, $SO_3^{2-}$, $Br^-$, $F^-$, $NO_2^-$, and $NO_3^-$.

In some embodiments, coloring agents may comprise oxides or salts of iron, terbium, erbium, chromium, cobalt and manganese. In one embodiment, coloring agents comprise at least one metallic salt of chromium, terbium, and manganese in the foil is of terbium chloride, chromium chloride, and manganese sulfate, respectively. The amount of coloring agent in a yttrium-containing composition may be approximately 0.05 wt % to approximately 2 wt %, or approximately 0.1 wt % to approximately 0.5 wt %, or approximately 0.07 wt % to approximately 1 wt %, based on the total weight of the yttrium-containing composition. Coloring liquids to be incorporated into yttrium-containing compositions may be prepared as aqueous coloring solutions having no solid colorant particles that are detectable at ambient temperature to the unaided eye after mixing a coloring agent with a solvent. Coloring agents suitable for use herein may include coloring liquids, described in commonly owned. U.S. Pat. Nos. 9,512,317, 9,365,459 and 9,095,403, each of which is hereby incorporated herein by reference in its entirety.

Ceramic materials may comprise zirconia ceramic material such as (unstabilized) zirconia or stabilized zirconia, where stabilized zirconia includes partially stabilized or fully stabilized zirconia. Examples of stabilized zirconia suitable for use herein include commercially available ceramic materials from Tosoh USA, such as zirconia that has been stabilized with yttria, (e.g., YSZ zirconia from Tosoh) including approximately 0.1 mol % to approximately 8 mol % yttria, or approximately 1 mol % yttria to approximately 3 mol % yttria or approximately 2 mol % yttria to approximately 7 mol % yttria, or approximately 2 mol % yttria to approximately 6 mol % yttria, or approximately 2 mol % yttria to approximately 5 mol % yttria, or approximately 3 mol % yttria to approximately 5 mol % yttria, or approximately 3 mol % yttria to approximately 4 mol % yttria, or approximately 4 mol % yttria to approximately 5 mol % yttria, or approximately 3.5 mol % yttria to approximately 5 mol % yttria.

Ceramic materials may comprise approximately 85 wt % to approximately 100 wt % zirconia or stabilized zirconia, based on the total weight of the zirconia ceramic material, or approximately 85 wt % or greater, or approximately 90 wt % or greater, or approximately 95 wt % or greater, or more than approximately 97 wt % or greater zirconia or stabilized zirconia, based on the total weight of the zirconia ceramic material. Other materials, such as, alumina may also be included in the zirconia ceramic material. Zirconia ceramic bodies may be formed from zirconia powder having a substantially uniform particle size distribution, such as powder with an average size in a range from approximately 0.005 micron (μm) to approximately 1 μm. Examples of ceramic material suitable for use herein also include zirconia described in commonly owned U.S. Pat. Nos. 8,298,329, 10,532,008, and 10,479,729, each of which is hereby incorporated herein by reference in its entirety.

Zirconia ceramic powder may be shaped as a block, disk, near net shape, or a form that approximates the size and/or shape of a single or multi-unit dental restoration, such as a crown, on-lay, bridge including a multi-unit bridge comprising restorations having more than one tooth structure, a partial or full solid-body denture, or a supporting structure such as an implant or an abutment. Porous zirconia ceramic bodies may be made by processes including but not limited to uniaxial or biaxial pressing or slip casting, and automated processes, including additive (e.g., 3-D printing) and subtractive (e.g., milling) automated processes. Processes for making ceramic bodies suitable for use herein include those described in commonly owned U.S. Pat. Nos. 9,365,459, 9,434,651, and 9,512,317, each of which is hereby incorporated herein by reference in its entirety. Commercially available pre-sintered or bisque stage ceramic bodies include those that have been heated to increase the density of a green body to below the full theoretical density of a fully sintered ceramic body in accordance with suggestions provided by the manufacturer. Pre-sintered ceramic bodies include those having a density of approximately 30% to 90%, or approximately 50% to 90%, of full theoretical density.

The pre-sintered ceramic bodies may be shaped in the form of a dental restoration either before or after application of the tantalum (or niobium) containing composition. Alternatively, after treating the porous ceramic bodies with a tantalum (or niobium) containing composition, the treated bodies may be sintered to approximately full theoretical density prior to milling into a final dental restoration. Examples of suitable shaped zirconia ceramic forms which may be treated and sintered to full theoretical density prior to shaping to a final dental restoration form may be found in commonly owned U.S. Pat. Nos. 9,597,265, D781,428, and D769, 449, each of which is hereby incorporated herein by reference in its entirety.

Unshaded (uncolored) or pre-colored ceramic powders that are shaded to match a target or desired shade in a final sintered body may be used to form the porous ceramic body. Commercially available ceramic blocks, such as BruxZir® Shaded 16 series porous ceramic bodies (Glidewell Laboratories, Irvine, Calif.) that match the VITA Classic shades in a final restoration may be used. Other pre-shaded ceramic powders are used for achieving a range of final dental shades in the sintered body, and the precise target shade is attained by additional coloring or staining before or after sintering.

Figure 2:
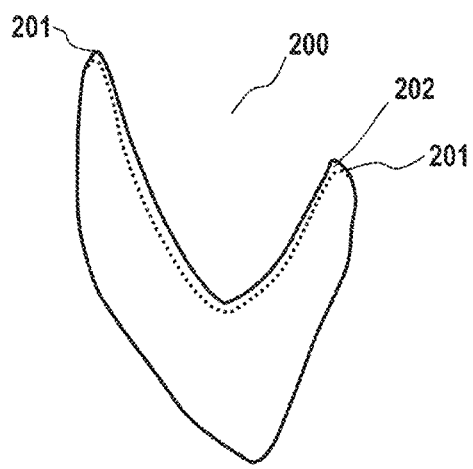
FIG. 2 is a cross-sectional illustration of a dental restoration.

Application techniques for applying the tantalum (or niobium) containing composition to penetrate the porous, pre-sintered ceramic bodies include, but are not limited to, painting, dipping, spraying, or infiltrating the ceramic body with the tantalum (or niobium) containing composition by other known application methods. The tantalum (or niobium) containing composition may be applied to penetrate regions of ceramic dental components that are susceptible to cracking or chipping. For example, in one embodiment, as illustrated in the cross-sectional view of a dental crown 200 of FIG. 2, the tantalum (or niobium) containing composition may penetrate the edge or a region of the crown, or the margin 201 that abuts the patient's gingiva. For example, where the tantalum (or niobium) containing composition is brushed or otherwise applied adjacent the margin edge 201, in the sintered body tantalum (or niobium) may penetrate to a depth 202 of approximately 0.5 mm to approximately 3 mm, or approximately 0.5 mm to approximately 4 mm, or approximately 0.5 mm to approximately 5 mm, or approximately 1 m to approximately 5 mm.

Accordingly, in some embodiments, a gradient of tantalum (or niobium) concentration is provided within the ceramic dental component with a higher tantalum (or niobium) concentration nearer to the surface and a lower tantalum (or niobium) concentration at an internal distance away from the surface. The tantalum (or niobium) concentration gradient provides a gradient of the physical properties (e.g., flexural strength, fracture toughness) within the body of the ceramic (e.g., zirconia) dental component. For example, in some embodiments, a sintered zirconia body having an yttria concentration of from 4-6 mot % that has been treated with a tantalum (or niobium) containing composition in the manner described herein may have a surface region with a fracture toughness that is greater than 4.0 $MPa \cdot m^{1/2}$, such as greater than 5.0 $MPa \cdot m^{1/2}$, such as greater than 6.0 $MPa \cdot m^{1/2}$, or greater than 7.0 $MPa \cdot m^{1/2}$, while having a fracture toughness at an interior region spaced internally from the surface region that is lower than the surface region fracture toughness and that is less than 4.0 $MPa \cdot m^{1/2}$, such as less than 3.0 $MPa \cdot m^{1/2}$, or less than 2.5 $MPa \cdot m^{1/2}$. In some embodiments, the surface region may occupy a depth of less than 1.0 trim from the outer surface of the zirconia body, such as a depth of less than 500 μm from the outer surface of the zirconia body, such as a depth of less than 250 μm from the outer surface of the zirconia body, such as a depth of less than 150 μm from the outer surface of the zirconia body, or a depth of less than 100 μm from the outer surface of the zirconia body.

In another embodiment, the tantalum (or niobium) containing composition may be applied to a region adjacent the attachment means of an implant supported denture. For example, the tantalum (or niobium) containing composition may be applied around a through hole of a screw retained denture. In other embodiments, where the dental restoration component comprises an implant or abutment, the entire ceramic body may be coated, for example by dipping in the tantalum (or niobium) containing composition to provide enhanced mechanical properties throughout the component.

In another embodiment, a porous single unit block, pre-form or near net shape may be dipped in a tantalum (or niobium) containing composition to achieve partial or complete penetration through the thickness of a body. In another embodiment, the tantalum (or niobium) containing composition may be applied to one or more sides or surfaces of a block, pre-form or near net shape, for partial penetration through the surface. In this embodiment, the porous ceramic bodies may be sintered after treatment with the tantalum (or niobium) containing composition, prior to milling or grinding to form a patient-specific dental restoration.

After sintering to approximately full theoretical density, treated, sintered ceramic bodies have enhanced mechanical properties without a reduction in translucency when compared to an untreated, sintered ceramic body comprising a substantially similar yttria-stabilized zirconia ceramic material.

Sintered zirconia ceramic bodies treated with a tantalum (or niobium) containing composition, according to the methods described herein, have flexural strengths greater than or equal to approximately 800 MPA, or greater than or equal to approximately 900 MPa, when measured according to the methods described herein.

In further embodiments, a damage resistant protective layer is created in a zirconia body such that the location and geometry of the protective layer can be controlled. The provision of a protective layer provides a capability of simultaneously manipulating mechanical properties such as fracture toughness and flexural strength by forming a tantalum or niobium-based selective diffusion protective coating layer (SDPCL) on the outer surface and inside of the zirconia body. The depth of the SDPC layer has characteristics that can be adjusted depending on the concentration of tantalum or niobium alkoxide and the concentration of added organic additives (e.g., polyvinyl pyrrolidone (PVP)). Damage resistant SDPCL diffuses toward the outer surface or into the bulk of zirconia to help mitigate crack propagation in the contact area of the sintered body.

Fractures in dental restorations are often caused by material failures. To reduce the fracture rate of dental restorations, it is important to understand the mechanism by which zirconia fractures. There are three classes of failure modes for single crowns, multi-unit bridges and full arches. The first of such are cracks (cone, median) or chips that occur at the occlusal surface of restorations. These type of failures are rare in full strength zirconia (3Y-TZP) devices. The second failure mode is via radial fracture which is often caused by tensile stresses at the cementation surface. This type of fracture is the primary mode of failure, and is responsible for more than 95% of failures in zirconia restorations. The third failure mode is due to operator error; though uncommon; and involve cracks on the anterior mandibular surface due to hand milling using diamond tools by dental technicians. In order to reduce fracture cases occurring in zirconia ceramic restorations, it is useful to mitigate cracking in their most vulnerable regions. For this, the brittleness of these regions may be reduced, fracture toughness and mechanical strength of the protected areas are increased, and fracture rates are thereby reduced.

Accordingly, in some embodiments, crack propagation is reduced or prevented by forming a selective diffusion protective coating layer (SDPCL) with high fracture toughness in the microstructure inside a zirconia body. To achieve this, a tantalum (or niobium) containing composition is applied to a porous bisque-fired zirconia prosthesis formed by CAD/CAM machining of a dental zirconia milling blank. Zirconia that can be treated by the tantalum (or niobium) containing composition may have yttria concentrations ranging between 3Y-TZP to 12Y-PSZ. In order to form an SDPCL within a zirconia body, a precursor containing tantalum alkoxide (or niobium alkoxide) is infiltrated into the bisque-fired porous zirconia body by dipping or painting before being sintered to maximal or near maximal density. By controlling the depth, thickness, location, and other size or geometric features of the SDPCL, it is possible to suppress crack propagation into the bulk microstructure of the zirconia even if damage is formed on the surface of the zirconia sintered body. It is further possible to improve the lifespan of the restoration by suppressing cracks and improving the mechanical strength.

Figure 5:
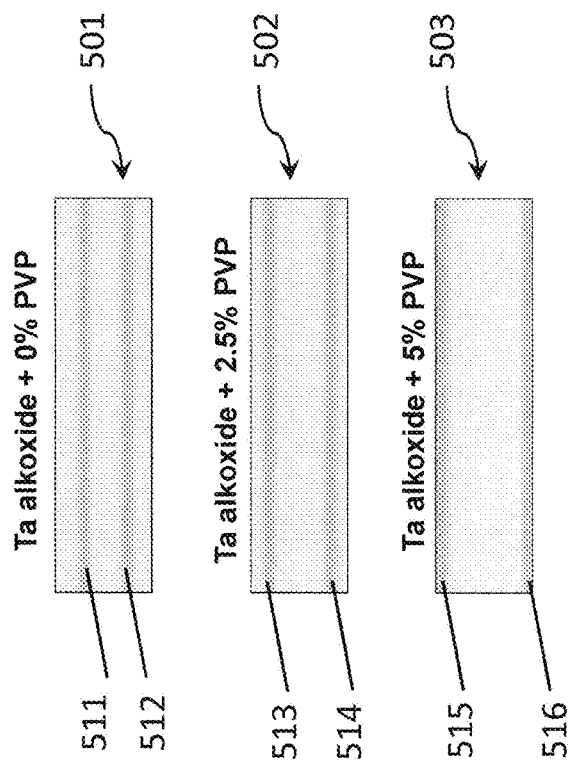
FIG. 5 is schematic diagrams showing exemplary selective diffusion protective coating layers (SDPCLs) located on or near the surface and internal structures of zirconia ceramic samples.

FIG. 5 contains examples of zirconia bodies (501, 502, and 503) having selective diffusion protective coating layers (SDPCLs) on their surfaces and internal structures that are obtained by treating the zirconia bodies with a tantalum (or niobium) containing composition. The first zirconia body 501 has been treated by applying a first tantalum containing composition (containing Ta alkoxide and 0% PVP) to the upper and lower surfaces of the first zirconia body 501, resulting in an upper SDPCL 511 and lower SDPCL 512 formed within the internal structure at relatively large distances from the upper and lower surfaces of the first zirconia body 501. Specifically, in the first zirconia body 501 embodiment shown in FIG. 5, the selective diffusion protective coating layers 511 and 512 comprise layers having a discrete thickness defined by an increased concentration of tantalum (or niobium) within the zirconia body. The SDPCL layers are thereby selectively located at a distance from the surfaces of the zirconia body 501, i.e., there is a region of low (to no) concentration of tantalum (or niobium) located above the upper SDPCL 511 and below the lower SDPCL 512 between the SDPCLs and their respective outer surfaces on the zirconia body 501. The remaining internal structure of the zirconia body 501 between the upper SDPCL 511 and the lower SDPCL 512 is also a region containing low (to no) concentration of tantalum (or niobium). In this way, the SDPCL regions 511, 512, which comprise the regions of the zirconia body 501 having enhanced physical properties (e.g., flexural strength and fracture toughness), can be selectively located at a position within the zirconia body 501 to achieve a desired performance or other objective.

The second zirconia body 502 has been treated by applying a second tantalum-containing composition (containing Ta alkoxide and 2.5% PVP) to the upper and lower surfaces of the second zirconia body 502, resulting in an upper SDPCL 513 and lower SDPCL 514 formed within the internal structure but relatively closer distances from the upper and lower surfaces of the second zirconia body 502. The third zirconia body 503 has been treated by applying a third tantalum-containing composition (containing Ta alkoxide and 5% PVP) to the upper and lower surfaces of the third zirconia body 503, resulting in an upper SDPCL 515 and lower SDPCL 516 formed within the internal structure but very near to the upper and lower surfaces of the third zirconia body 503.

As demonstrated by the examples shown in FIG. 5, the depth of the SDPC layer in the zirconia structure has a characteristic that can be adjusted according to the concentration of the tantalum alkoxide (or niobium alkoxide) and the added organic additive (i.e., PVP). The tantalum-containing compositions having low (or no) concentrations of organic additive (i.e., PVP) provide an SDPC layer at relatively deeper locations away from the treated surfaces. The tantalum-containing compositions having relatively higher concentrations of organic additive (i.e., PVP) provide an SDPC layer at relatively shallower locations, nearer to the treated surfaces. As a result, the SDPCL of zirconia obtained by treating the zirconia with a tantalum (or niobium) containing composition has a barrier property capable of suppressing the propagation of cracks into the microstructure inside the zirconia due to the layered structure and characteristics of high fracture toughness provided by the SDPCL. This is advantageous because the protective coating layer formed on the surface of the zirconia restoration by a treatment with a tantalum (or niobium) containing composition can be partially damaged by additional hand milling processes by dental technicians, and consequently can cause the formation of crack propagation in the restoration.

For example, in the finishing process of a final sintered multi-unit zirconia anterior restoration, dental technicians use a diamond wheel to create a sharp line on the mandibular surface of the anterior teeth. At this time, flaws occur on the mandibular surface, which may cause catastrophic failure of the restoration. In another example, a final sintered zirconia restoration is subjected to a glazing process followed by a sandblasting process on the cementation surface. At this time, flaws occur on the cementation surface and are easily propagated by slow-crack-growth mechanisms from conditions existing in the patient's oral environment which can cause catastrophic failure of the restoration. Another example is that in zirconia full arch restorations, flaws may exist in the area of the screw retaining hole, leading to failure of the final zirconia full arch restoration. Because the edge of the screw retaining hole is a stress concentrator, cracks can be easily initiated under high loads. The controlled location and enhanced strength and toughness characteristics of the SDPCLs shown in FIG. 5 provide a capability of suppressing the propagation of cracks into the microstructure inside these zirconia restorations.

Test Methods

Density

The density strongly depends on the composition and structure of the samples of the ceramic materials. Density calculations for ceramic bodies may be determined by liquid displacement method of Archimedes principle. Distilled water was used as the liquid medium. Density of ceramic samples were calculated using the following formula:

$$\rho = \frac{(W^2 - W^1)}{(W^4 - W^1) - (W^3 - W^2)}$$

ρ=Density (gram/cc);
W1=Weight of empty specific gravity bottle (gram);
W2=Weight of specific gravity bottle with sample (gram);
W3=Weight of specific gravity bottle with sample and distill water (gram);
W4=Weight of specific gravity bottle with distill water (gram).

3-Point Flexural Strength Test (Bars)

Flexure tests were performed on sintered test materials using ISO 6872 guidelines for preparation of strength testing for dental ceramic, flexural strength bar were milled and prepared. Once prepared, the bars were placed centrally on the bearers of the test machine so the load applied to a 4 mm wide face was along a line perpendicular to the long axis of the test piece center. Then force is applied and the load needed for breaking the test piece (loading rate was 0.5 mm/min) was recorded. The flexural strength is calculated using sample's dimensional parameter and critical load information.

Flexural strength, σ, in MPa was calculated according to the following formula:

$$\sigma = \frac{3Pl}{2Wb^2}$$

where P is the breaking load, in newton; l is the test span (center-to-center distance between support rollers), in millimeters; w is the width of the specimen, i.e. the dimension of the side at right angles to the direction of the applied load, in millimeters; b is the thickness of the specimen, i.e. the dimension of the side parallel to the direction of the applied load, in millimeters. The mean and standard deviation of the strength was reported. Test bars were prepared by cutting bisque materials taking into consideration the targeted dimensions of the sintered test bars and the enlargement factor (E.F.) of the material, as follows:

starting thickness=3 mm×E.F.;
starting width=4 mm×E.F.;
starting length=35 mm×E.F.

The cut, bisque bars were sintered and flexural strength data was measured and calculated according to the 3 point flexural strength test described in ISO (International Standard) 6872 Dentistry—Ceramic Materials.

3-Unit Bridge Critical Load Test

Figure 12B:
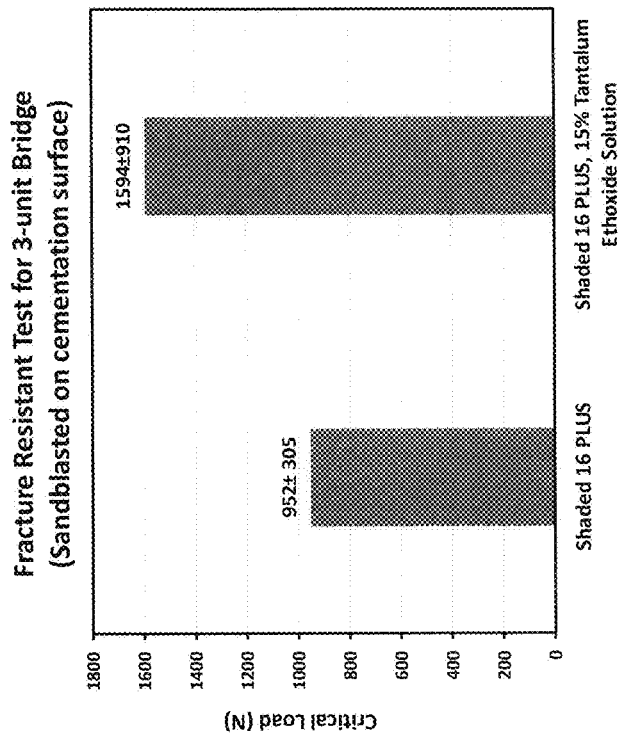
FIG. 12A is an illustration of a method for measuring the fracture resistance for a 3-unit bridge dental restoration.
Figure 12A:
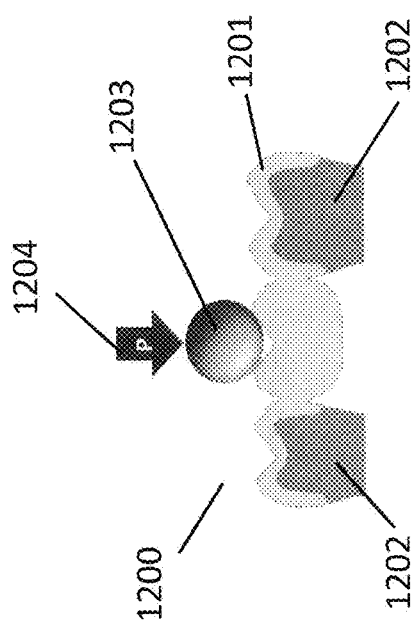

Referring to FIG. 12A, critical load tests were performed on 3-unit bridge samples 1201 (tooth numbers 29, 30, and 31) using a universal electromechanical test frame 1200 (model EZ-LX, Shimadzu Scientific Instruments, Kyoto, Japan). A 4.5 mm diameter tungsten carbide (WC) ball 1203 was used as the indenter. The bridge metal dies 1202 of a dentition model were used as the basis for design of the samples, and also used as the support for the load test. The prepared bridge samples 1201 were placed on the dentition model metal dies 1202 and the WC ball 1203 indenter was located in the center of the occlusal surface of the pontic of the three-unit bridge. A load 1204 was applied, and load speed was fixed at 0.6 mm/min.

Biaxial Strength Test (Piston-On-Three-Ball Test)

Universal mechanical testing machine, capable of a crosshead speed of 1 mm/min (±0.5) and an ability to measure applied loads of between 10 N and 2 500 N (±1%) was used.

The Biaxial flexural strength test fixture had a sample test support of three hardened steel balls with a diameter of (4.5±2) mm positioned 120° apart on a support circle with a diameter of (11±1) mm. The sample was placed concentrically on these supports and the load was applied with a flat punch with a diameter of (1.4±0.2) mm at the center of the sample specimen. The experiment was conducted according to the test method described in ISO (International Standard) 6872 Dentistry—Ceramic Materials.

Vickers Hardness Test

Vickers Hardness Test conditions were as follows: 19.6 N (2,000 gf) with a Load for 10 sec. Micro-indentation hardness testing was performed according to In H. Kuhn & D. Medlin (Eds.), ASM Handbook, Volume 8: Mechanical Testing and Evaluation (pp. 221-231). ASM International).

A diamond in the form of a square-based pyramid was used as the indenter shape to produce geometrically similar impressions, irrespective of size; the impression should have well-defined points of measurement; and the indenter should have high resistance to self-deformation.

Figure 3:
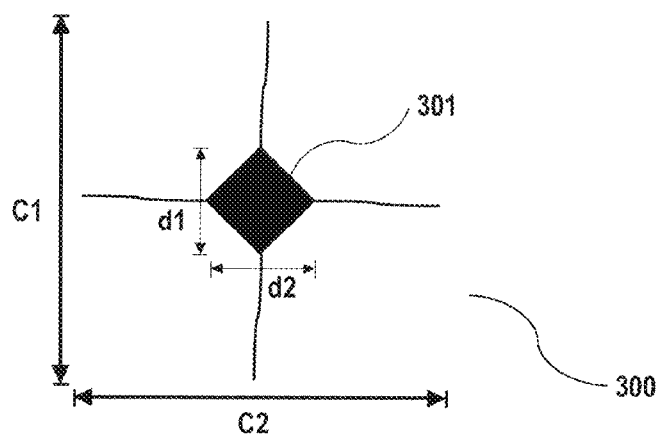
FIG. 3 is a schematic representation of Vickers hardness indenter impression shape.

With reference to the schematic representation of a testing indentation (300) in FIG. 3, an impression (301) is observed for $d_1$=vertical indentation length; $d_2$=horizontal indentation length; $c_1$=vertical length spanned by indentation cracks; $c_2$=horizontal length spanned by indentation cracks; d=average indentation length; c=average length spanned by indentation cracks.

Hardness was calculated as: $H_{(hardness)}=1.854*P/d^2$ where P is the applied load in Newton (N) and d is the arithmetic mean of the two diagonals ($d_1$ and $d_2$) in micrometers. The hardness can then be converted into GPa as follows: H (GPa)=0.009817HV. (Ref: Vander, G. F. (2000). Micro-indentation hardness testing was performed according to In H. Kuhn & D. Medlin (Eds.), ASM Handbook, Volume 8: Mechanical Testing and Evaluation (pp. 221-231). ASM International).

Fracture Toughness from indentation method (Indentation Toughness) was calculated from the Hardness values, as follows:

$$K_{IC} = 0.016\sqrt{\frac{E}{H}} \times \frac{P}{C^{\frac{3}{2}}}$$

where $K_{Ic}$=Fracture Toughness (MPa m$^{1/2}$); E=Young's Modulus (GPa); H=Hardness (GPa); L=load (N); and C=average crack length (m). (Ref. Evaluation of Indentation Techniques for Measuring Fracture Toughness: I, Direct Crack Measurements, J. Am. Ceram., 64(9), pp 533-538, 1981, incorporated herein by reference)

Translucency

Translucency was measured as percent light transmittance. Sample wafers were sectioned from a bisque stage block and machined to a diameter that approximates a final diameter of approximately 30 mm after sintering. Wafers were ground flat until visually free of defects with 1200 and 2000 grit SiC polishing paper. Surface dust was removed and the samples were sintered according to the sintering profile(s) described herein. The final thickness of the bisque body corresponded to a target thickness of approximately 1.0 mm after sintering.

After sintering, sample wafers were briefly washed with isopropanol to remove errant surface material; however, no further surface preparation techniques were applied to the samples prior to testing. Transmission spectra were measured between the wavelengths of 360 nm to 740 nm with a Konica-Minolta CM5 spectrophotometer illuminated by a D65 light source. The spectrophotometer was calibrated to white and black prior to measurement. Translucency samples were placed flush against the (approximately) 24 mm integrating sphere aperture. A minimum of four spectra were collected per sample and averaged to yield a final transmission spectra. Where noted, transmission spectra were corrected for deviations in sample thickness.

Color Space (CIE L*a*b*) Test

Zirconia materials were measured for color space according to CIE L*a*b* (International Commission on Illumination, measuring two polar axes for color, 'a' and 'b', and value (lightness, L)) values using a Konica Minolta Spectrometer with a D65 light source.

30 mm diameter sintered circular test wafers were cut from pre-sintered bisque blocks. The targeted final thickness of the test wafers after sintering was 1.0 mm. Therefore, the starting thickness for each wafer was calculated based on the targeted final thickness taking into consideration the enlargement factor (EF) as follows:

Final thickness×(EF)=bisque wafer thickness.

To measure color, the Konica Minolta Spectrometer was set on reflectance mode, and the L*a*b* values of the sample were measured. These values were referenced to materials made from traditional processes. Color equivalence is indicated if a comparison of ceramic samples made by the methods described herein and traditional methods have a ΔE of less than approximately 3 or less, approximately 2.5 or less, or approximately 2 or less.

EXAMPLES

Tantalum-Containing Compositions 1-3

Tantalum-containing compositions were prepared according to the compositions of Table 1.

TABLE 1

Tantalum-Containing Compositions 1-3

| Composition Number | Tantalum Source (Wt %) | Solvent (Wt %) | Polymer (Wt %) |
|---|---|---|---|
| 1 | Tantalum ethoxide (10%) | Acetone (89.8%) BA (0.02%) | PVB (0.17%) |

TABLE 1-continued

Tantalum-Containing Compositions 1-3

| Composition Number | Tantalum Source (Wt %) | Solvent (Wt %) | Polymer (Wt %) |
|---|---|---|---|
| 2 | Tantalum ethoxide (30%) | Acetone (69.1%) BA (0.10%) | PVB (0.8%) |
| 3 | Tantalum ethoxide (50%) | Acetone (49.3%) BA (0.10%) | PVB (0.6%) |

BA—Butyraldehyde
PVB—Polyvinyl Butyral

Examples 1-3

Bisque stage zirconia ceramic bodies were treated with a tantalum-containing compositions, sintered and tested for mechanical properties.

Sample wafers were milled from porous, pre-sintered BruxZir® HT zirconia milling blanks (unshaded 3Y-TZP) to target a thickness of approximately 1 mm after sintering.

The tantalum-containing compositions described in Table 1 were brush applied to the sample wafers, then dried, and sintered (substantially according to manufacturer-provided instructions of the zirconia blocks) to approximately full theoretical density. The sample wafers were then tested for indentation toughness. The results are shown in Table 2 below.

TABLE 2

Indentation Toughness for Treated Samples

| Ex. # | Tantalum-Containing Composition Number | Indentation Toughness (MPa $M^{1/2}$) |
|---|---|---|
| 1 | Composition 1 | 7.67 |
| 2 | Composition 2 | 9.1 |
| 3 | Composition 3 | 11.8 |
| CE1 | Untreated | 5.24 |

The results in Table 2 demonstrate that the zirconia samples treated with the tantalum-containing compositions show a higher range of indentation toughness as compared to the untreated sample.

Tantalum-Containing Compositions 4-6

Tantalum-containing compositions were prepared according to the compositions of Table 3.

TABLE 3

Tantalum-Containing Compositions 4-7

| Composition Number | Tantalum Source (Wt %) | Solvent (Wt %) | Polymer (Wt %) |
|---|---|---|---|
| 4 | Tantalum ethoxide (10%) | Acetone (89.5%) BA (0.10%) | PVB (0.4%) |
| 5 | Tantalum ethoxide (30%) | Acetone (68.8%) BA (0.60%) | PVB (0.6%) |
| 6 | Tantalum ethoxide (50%) | Acetone (49.5%) BA (0.10%) | PVB (0.4%) |
| 7 | Tantalum ethoxide (50%) | Isopropanol (49%) | PVP (1%) |
| 8 | Tantalum ethoxide (60%) | Isopropanol (34%) Methanol (5%) | PVP (1%) |

BA—Butyraldehyde
PVB—Polyvinyl Butyral
PVP—Polyvinyl Pyrollidone

Examples 4-8

Bisque stage zirconia ceramic bodies were treated with a tantalum-containing compositions, sintered and tested for mechanical properties.

Sample wafers were milled from porous, pre-sintered BruxZir® Esthetic zirconia milling blanks (A2 shade 4.9YSZ) to target a thickness of approximately 3 mm after sintering. Other test samples, such as flexural or biaxial strength samples, were machined to the appropriate test dimensions.

The tantalum-containing compositions described in Table 3 were brush applied to the samples, then dried, and sintered (substantially according to manufacturer-provided instructions of the zirconia blocks) to approximately full theoretical density. The sample wafers were then tested for indentation toughness, while the other samples were tested for 3-point bend strength and biaxial strength. The results are shown in Table 4 below.

TABLE 4

Fracture Toughness, Flexural Strength, and Biaxial Strength for Examples 4-8

| Ex. # | Tantalum-Containing Composition Number | indentation Toughness (MPa $M^{1/2}$) | 3-Point Bend Strength (MPa) | Biaxial Strength (MPa) |
|---|---|---|---|---|
| 4 | Composition 4 | 3.22 | 955 | 1291 |
| 5 | Composition 5 | 7.62 | 1005 | 1510 |
| 6 | Composition 6 | 9.75 | 1194 | 1558 |
| 7 | Composition 7 | 9.78 | 1070 | |
| 8 | Composition 8 | 10.66 | 1002 | |
| CE2 | Untreated | 2.59 | 807 | 1202 |

The results in Table 4 demonstrate that the zirconia samples treated with the tantalum-containing compositions show a higher range of indentation toughness, 3-point bend strength, and biaxial strength as compared to the untreated sample.

Examples 9-13

Bisque stage zirconia ceramic bodies were treated with a tantalum-containing compositions, sintered and tested for optical properties.

Sample wafers (36 mm diameter circular wafers) were milled from porous, pre-sintered BruxZir® Esthetic zirconia milling blanks (4.9YSZ) to target a thickness of approximately 1 mm after sintering.

The tantalum-containing compositions described in Table 6 were brush applied to the sample wafers, then dried, and sintered (substantially according to manufacturer-provided instructions of the zirconia blocks) to approximately full theoretical density. The sample wafers were then tested for translucency loss and color change. The results are shown in Table 6 below.

TABLE 6

Translucency Loss and Color Change for Treated Samples

| Ex. # | Tantalum-Containing Composition Number | Zirconia Milling Blank Shade | Translucency Loss (−%T) Relative to Untreated Sample | Color Change (ΔE) Relative to Untreated Sample |
|---|---|---|---|---|
| 9 | 8 | Bleach (BL) | −1.26% | 2.2 |
| 10 | 8 | B1 | −1.89% | 1.68 |
| 11 | 8 | A1 | −1.61% | 1.57 |
| 12 | 8 | A3.5 | | 1.21 |
| 13 | 8 | White (W) | −1.83% | 1.57 |

The results in Table 6 demonstrate that the zirconia samples treated with the tantalum-containing compositions show only slight changes in translucency and shade compared to untreated sample wafers.

Example 14

Bisque stage zirconia ceramic bodies were treated with tantalum-containing compositions, sintered and tested for optical properties.

Sample wafers were milled from porous, pre-sintered BruxZir® Esthetic zirconia milling blanks (white, std. 4.9YSZ) to target a thickness of approximately 1 mm after sintering.

Tantalum-containing composition number 8 described in Table 3 was brush applied to the sample wafers, then dried, and sintered (substantially according to manufacturer-provided instructions of the zirconia blocks) to approximately full theoretical density. Comparative sample wafers (CE3 and CE4) were also prepared from porous, pre-sintered BruxZir® Esthetic zirconia milling blanks (white, std. 4.9YSZ) and BruxZir® HT 2.0 zirconia milling blanks (white, std. 3Y-TZP), which were left untreated. The sample wafers were then tested for optical transmission over a range of wavelengths, with the full results reproduced in FIG. 4, which shows the results for the Example 14 wafer 401, the CE3 wafer 402, and the CE4 wafer 403. The results for light transmission at a wavelength of 700 nm are shown in Table 7 below.

TABLE 7

Translucency Loss and Color Change for Treated Samples

| Ex. # | Tantalum-Containing Composition Number | Zirconia Milling Blank Yttria Content | Zirconia Milling Blank Shade | Transmission (%) at 700 nm wavelength |
|---|---|---|---|---|
| 14 | 8 | 4.9 YSZ | White (W) | 55.8 |
| CE3 | Untreated | 4.9 YSZ | White (W) | 56.7 |
| CE4 | Untreated | 3Y-TZP | White (W) | 50.4 |

Figure 4:
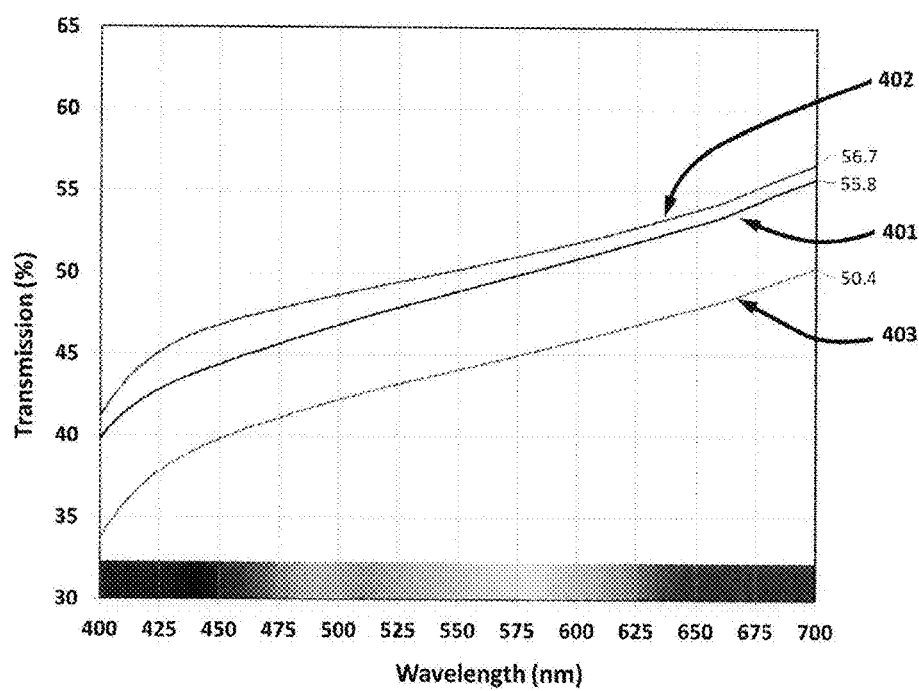
FIG. 4 is a graphical representation of transmittance over a wavelength range.

The results in FIG. 4 and Table 7 demonstrate that the Example 14 zirconia sample (4.9 YSZ) treated with the tantalum-containing composition shows only a slight change in translucency at 700 nm wavelength as compared to the untreated 4.9 YSZ sample wafer (CE3), and that it is approximately 12% more translucent than the untreated 3 YSZ sample wafer (CE4).

Example 15

Bisque stage zirconia ceramic three-unit bridge samples were prepared for critical load testing. Sample bridges were designed from a standard dentition model and milled from porous, pre-sintered zirconia milling blanks.

One set of samples (BruxZir® Esthetic, std. 4.9YSZ) was treated by brush application with tantalum-containing composition number 8 described in Table 3, then dried. Comparative sample three-unit bridges (CE5, CE6, and CE7) were also prepared from porous, pre-sintered zirconia milling blanks (BruxZir® Shaded 16 Plus, std. 3Y-TZP; BruxZir® Esthetic, std. 4.9YSZ; and Katana® UTML, std. 5YSZ) and were left untreated. The sample bridges were sintered according to the manufacturer recommended sintering profile. After sintering, all samples were sandblasted with 50 μm alumina particles under 60 psi pressure, cleaned with compressed air and tested. All sandblasted three-unit bridge specimens were glazed at a temperature between 870° C. and 1050° C.

The three-unit bridge samples then underwent critical load testing, with the full results reproduced in Table 8 below.

TABLE 8

Three-Unit Bridge Critical Load Testing Results

| Ex. # | Tantalum-Containing Composition Number | Zirconia Milling Blank Yttria Content | Three-Unit Bridge Critical Load (N) | Standard Deviation |
|---|---|---|---|---|
| 15 | 8 | 4.9Y-PSZ | 2427 | 938 |
| CE5 | Untreated | 3Y-TZP | 846 | 563 |
| CE6 | Untreated | 4.9Y-PSZ | 821 | 318 |
| CE7 | Untreated | 5Y-PSZ | 416 | 188 |

The results in Table 8 demonstrate that the zirconia three-unit bridge samples treated with the tantalum-containing composition show a higher range of critical load as compared to the untreated samples.

Example 16

Specimens comprising zirconia restorations 600 like those shown in FIG. 6 were prepared from a 3Y-TZP zirconia material. A first sample restoration 600 was left untreated. Three additional sample restorations 600 were treated with tantalum-containing compositions comprising: 15 wt % tantalum alkoxide, 20 wt % tantalum alkoxide, and 25 wt % tantalum alkoxide, respectively. Each of the tantalum-containing compositions contained 0 wt % of the organic additive (i.e., PVP). The tantalum-containing compositions were applied to all exposed surfaces of the sample restorations. The sample restorations 600 were then sintered at 1530° C. for 2.5 hours.

Each sample restoration was cut along the line 601 to expose the internal structure of the zirconia restoration. After cutting and preparing each sample, a micro indentation test was performed at multiple locations on the internal structure of the restoration (see 602) using a diamond indenter (19.8N) to confirm the change in fracture toughness according to the treatment by the tantalum-containing composition. The results are shown in the graphs contained in FIG. 7A (untreated sample), FIG. 7B (sample treated with 15 wt % tantalum alkoxide and no PVP), FIG. 7C (sample treated with 20 wt % tantalum alkoxide and no PVP), and FIG. 7D (sample treated with 25 wt % tantalum alkoxide and no PVP).

It is observed that the zirconia body of the untreated sample (FIG. 7A) had a relatively constant fracture toughness property at each test location through the thickness of the dental restoration. On the other hand, the samples treated with tantalum-containing compositions were provided with selective diffusion protective coating layers (SDPCLs) due to the higher concentration of tantalum at locations within the sample body. Higher fracture toughness measurements were observed at the locations of the SDPCLs in the treated samples, with the highest fracture toughness values being observed in the samples treated with the tantalum-containing compositions having the highest concentration of tantalum alkoxide (FIG. 7D).

Example 17

Specimens comprising zirconia restorations 600 like those shown in FIG. 6 were prepared from a 3Y-TZP zirconia material. Three sample restorations 600 were treated with tantalum-containing compositions comprising: 15 wt % tantalum alkoxide and 0 wt % PVP, 15 wt % tantalum alkoxide and 2.5 wt % PVP, and 15 wt % tantalum alkoxide and 5 wt % PVP, respectively. The tantalum-containing compositions were applied to all exposed surfaces of the sample restorations. The sample restorations 600 were then sintered at 1530° C. for 2.5 hours.

Figure 8A:
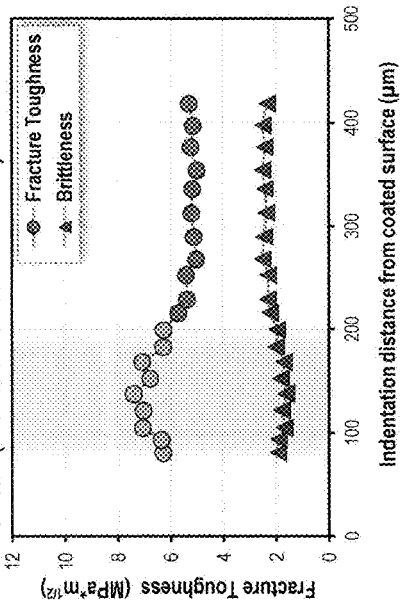
Figure 8B:
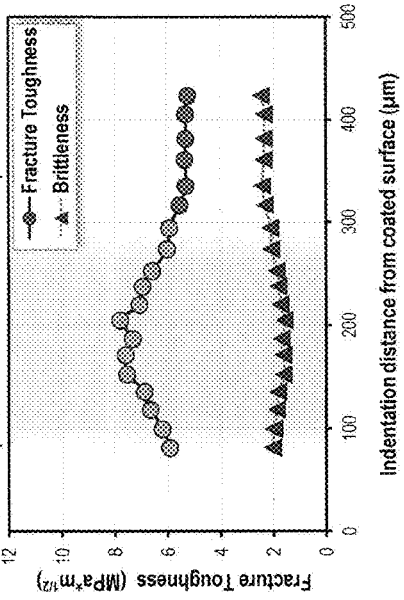
Figure 8C:
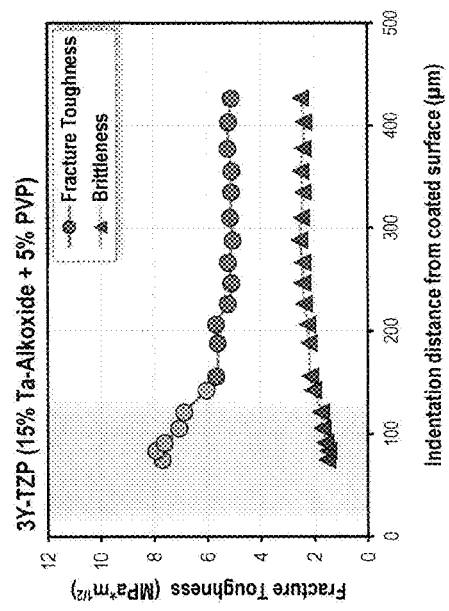

Each sample restoration was cut along the line 601 to expose the internal structure of the zirconia restoration. After cutting and preparing each sample, a micro indentation test was performed at multiple locations on the internal structure of the restoration (see 602) using a diamond indenter (19.8N) to confirm the change in fracture toughness according to the treatment by the tantalum-containing composition. The results are shown in the graphs contained in FIG. 8A (sample treated with 15 wt % tantalum alkoxide and 0 wt % PVP), FIG. 8B (sample treated with 15 wt % tantalum alkoxide and 2.5 wt % PVP), FIG. 8C (sample treated with 15 wt % tantalum alkoxide and 5 wt % PVP).

Each of the samples treated with tantalum-containing compositions were provided with selective diffusion protective coating layers (SDPCLs) due to the higher concentration of tantalum at locations within the sample body. Higher fracture toughness measurements were observed at the locations of the SDPCLs in the treated samples. The location of the SDPCL in each sample was different, which difference is attributable to the concentration of PVP contained within the tantalum-containing composition. In particular, the sample treated with a tantalum-containing composition having 0 wt % PVP (see FIG. 8A) provided an SDPCL located at a distance from 100-300 μm from the surface of the zirconia restoration body. The sample treated with a tantalum-containing composition having 2.5 wt % PVP (see FIG. 8B) provided an SDPCL located at a distance from 75-200 μm from the surface of the zirconia restoration body. Finally, the sample treated with a tantalum-containing composition having 5 wt % PVP (see FIG. 8C) provided an SDPCL located at a distance from 0-150 μm from the surface of the zirconia restoration body. Accordingly, the depth of the SDPCL for the treated samples was controlled by adjusting the concentration of the organic additive (i.e., PVP) in the tantalum-containing composition.

Example 18

Specimens comprising zirconia restorations 600 like those shown in FIG. 6 were prepared from a 4Y-PSZ zirconia material. Three sample restorations 600 were treated with tantalum-containing compositions comprising: 30 wt % tantalum alkoxide and 0 wt % PVP, 30 wt % tantalum alkoxide and 2.5 wt % PVP, and 30 wt % tantalum alkoxide and 5 wt % PVP, respectively. The tantalum-containing compositions were applied to all exposed surfaces of the sample restorations. The sample restorations 600 were then sintered at 1530° C. for 2.5 hours.

Figure 9A:
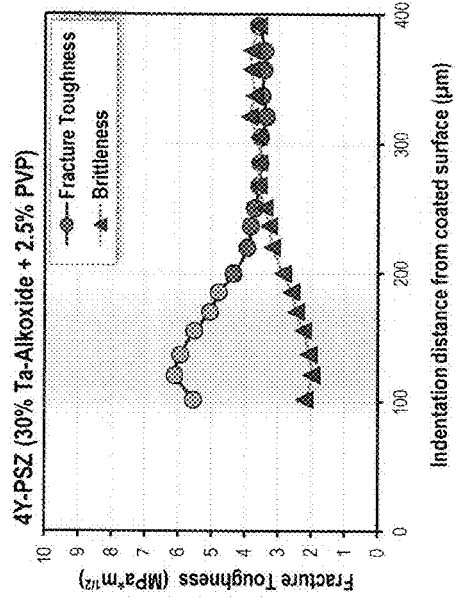
Figure 9B:
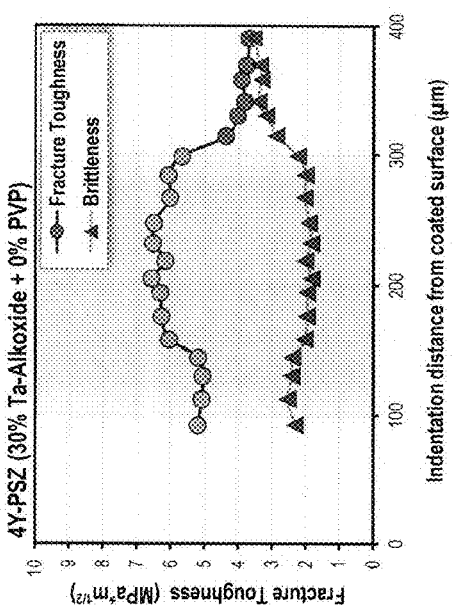
Figure 9C:
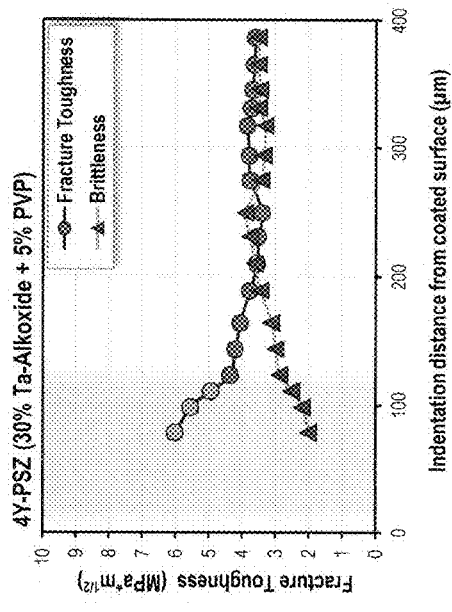

Each sample restoration was cut along the line 601 to expose the internal structure of the zirconia restoration. After cutting and preparing each sample, a micro indentation test was performed at multiple locations on the internal structure of the restoration (see 602) using a diamond indenter (19.8N) to confirm the change in fracture toughness according to the treatment by the tantalum-containing composition. The results are shown in the graphs contained in FIG. 9A (sample treated with 30 wt % tantalum alkoxide and 0 wt % PVP), FIG. 9B (sample treated with 30 wt % tantalum alkoxide and 2.5 wt % PVP), FIG. 9C (sample treated with 30 wt % tantalum alkoxide and 5 wt % PVP).

Each of the samples treated with tantalum-containing compositions were provided with selective diffusion protective coating layers (SDPCLs) due to the higher concentration of tantalum at locations within the sample body. Higher fracture toughness measurements were observed at the locations of the SDPCLs in the treated samples. The location of the SDPCL in each sample was different, which difference is attributable to the concentration of PVP contained within the tantalum-containing composition. In particular, the sample treated with a tantalum-containing composition having 0 wt % PVP (see FIG. 9A) provided an SDPCL located at a distance from 100-300 μm from the surface of the zirconia restoration body. The sample treated with a tantalum-containing composition having 2.5 wt % PVP (see FIG. 9B) provided an SDPCL located at a distance from 75-200 μm from the surface of the zirconia restoration body. Finally, the sample treated with a tantalum-containing composition having 5 wt % PVP (see FIG. 9C) provided an SDPCL located at a distance from 0-150 μm from the surface of the zirconia restoration body. Accordingly, the depth of the SDPCL for the treated samples was controlled by adjusting the concentration of the organic additive (i.e., PVP) in the tantalum-containing composition.

Example 19

Specimens comprising zirconia restorations 600 like those shown in FIG. 6 were prepared from a 5Y-PSZ zirconia material. Three sample restorations 600 were treated with tantalum-containing compositions comprising: 45 wt % tantalum alkoxide and 0 wt % PVP, 45 wt % tantalum alkoxide and 2.5 wt % PVP, and 45 wt % tantalum alkoxide and 5 wt % PVP, respectively. The tantalum-containing compositions were applied to all exposed surfaces of the sample restorations. The sample restorations 600 were then sintered at 1530° C. for 2.5 hours.

Figure 10A:
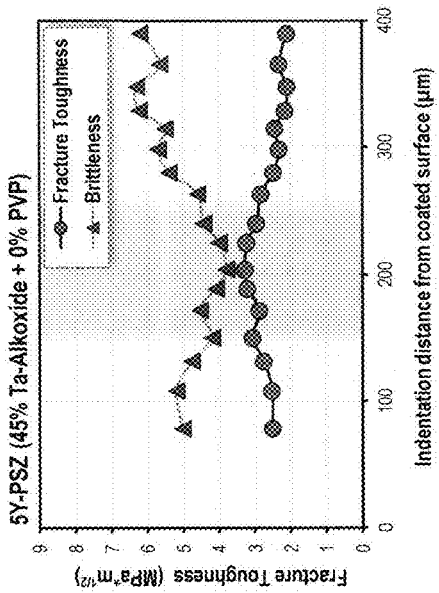
Figure 10B:
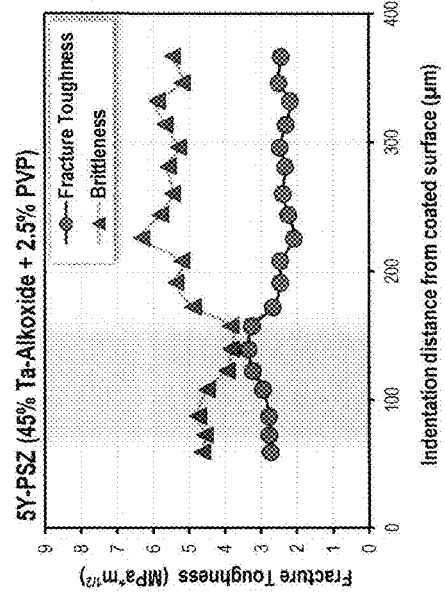
Figure 10C:
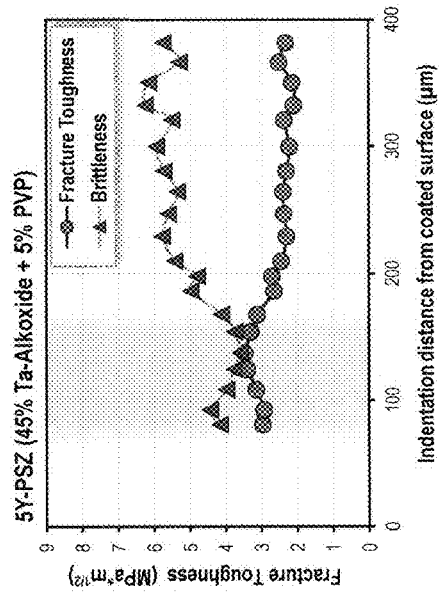

Each sample restoration was cut along the line 601 to expose the internal structure of the zirconia restoration. After cutting and preparing each sample, a micro indentation test was performed at multiple locations on the internal structure of the restoration (see 602) using a diamond indenter (19.8N) to confirm the change in fracture toughness according to the treatment by the tantalum-containing composition. The results are shown in the graphs contained in FIG. 10A (sample treated with 45 wt % tantalum alkoxide and 0 wt % PVP), FIG. 10B (sample treated with 45 wt % tantalum alkoxide and 2.5 wt % PVP), FIG. 10C (sample treated with 45 wt % tantalum alkoxide and 5 wt % PVP).

Each of the samples treated with tantalum-containing compositions were provided with selective diffusion protective coating layers (SDPCLs) due to the higher concentration of tantalum at locations within the sample body. Higher fracture toughness measurements were observed at the locations of the SDPCLs in the treated samples. The location of the SDPCL in each sample was different, which difference is attributable to the concentration of PVP contained within the tantalum-containing composition. In particular, the sample treated with a tantalum-containing composition having 0 wt % PVP (see FIG. 10A) provided an SDPCL located at a distance from 150-270 μm from the surface of the zirconia restoration body. The sample treated with a tantalum-containing composition having 2.5 wt % PVP (see FIG. 10B) provided an SDPCL located at a distance from 60-180 μm from the surface of the zirconia restoration body. Finally, the sample treated with a tantalum-containing composition having 5 wt % PVP (see FIG. 10C) provided an SDPCL located at a distance from 50-160 μm from the surface of the zirconia restoration body. Accordingly, the depth of the SDPCL for the treated samples was controlled by adjusting the concentration of the organic additive (i.e., PVP) in the tantalum-containing composition.

Example 20

It was observed that the sintering conditions for the zirconia body will also have an effect on the depth of an SDPCL formed in the sintered body that had been treated with a tantalum-containing composition. In particular, a longer sintering time will tend to cause the tantalum to diffuse deeper within the treated body to provide an SDPCL layer at a deeper location within the body.

Specimens comprising a zirconia block 1100 like that shown in FIG. H A were prepared from a 4.9Y-TLP zirconia material. Sample blocks 1100 were treated with a tantalum-containing composition comprising 50 wt % tantalum alkoxide and 1 wt % PVP. The tantalum-containing compositions were applied to all exposed surfaces of the sample restorations. The sample blocks 1100 were then sintered at 1530° C. for 20 hours.

Figure 11B:
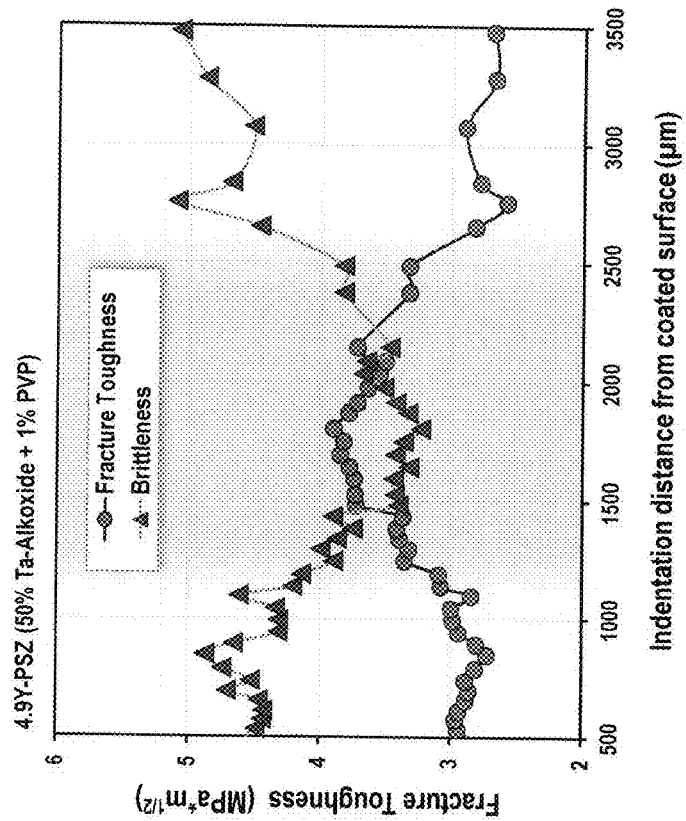
FIG. 11B is a graph showing fracture toughness and brittleness values for the zirconia block of FIG. 11A at locations having selected distances from the coated surface of the zirconia block.
Figure 11A:
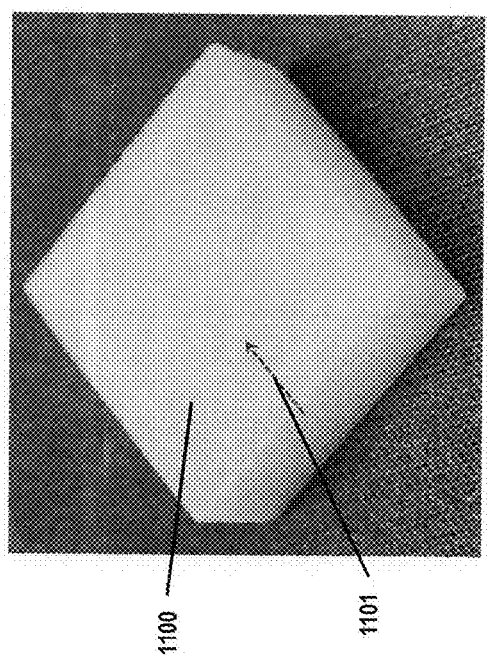
FIG. 11A is an image of a zirconia block.

Each sample block 1100 was cut along the line 1101 to expose the internal structure of the zirconia block. After cutting and preparing each sample, a micro indentation test was performed at multiple locations on the internal structure of the block 1100 using a diamond indenter (19.8N) to confirm the change in fracture toughness according to the treatment by the tantalum-containing composition. The results are shown in the graph contained in FIG. 11B.

Each of the sample blocks treated with tantalum-containing compositions were provided with a selective diffusion protective coating layer (SDPCL) due to the higher concentration of tantalum at locations within the sample block body. Higher fracture toughness measurements were observed at the location of the SDPCL in the treated samples. The SDPCL was observed to be located at a distance of from 1000 μm to 2500 μm from the outer surface, which was observed to be a much larger depth in comparison the samples sintered for a shorter period of time (2.5 hours).

Example 21

It was observed that treatment of a 3-unit bridge with a tantalum-containing composition will significantly increase the fracture resistance of the dental restoration.

Specimens comprising a 3-unit bridge 1200 like that shown in FIG. 12A were prepared from a 3Y-TZP zirconia material (BruxZir® Shaded 16 Plus, Glidewell Laboratories). A first sample bridge unit 1200 was left untreated, and a second was treated with a tantalum-containing composition comprising 15 wt % tantalum ethoxide. The tantalum-containing compositions was applied to all exposed surfaces of the second sample bridge unit 1200. The sample bridge units 1200 were then sintered at 1580° C. for 2.5 hours, treating with a glaze at 800-850° C., and then sandblasting the cemented surface at about 60 psi with 50 micron-sized alumina sand.

Each sample bridge unit 1200 was tested for fracture resistance according to the methods described herein. The results are shown in the graph provided in FIG. 12B. The sample bridge unit 1200 treated with a tantalum-containing composition was observed to provide a significantly higher fracture resistance when compared to the untreated bridge unit 1200.

Examples 22-24

Sample specimens of zirconia materials were prepared and tested for flexural strength according to ISO 6872 (2015) as described herein. Samples were also tested for surface fracture toughness. The results are shown in the tables contained in FIGS. 13-15.

In FIG. 13, the zirconia specimens each were prepared from a 3Y-TZP material and were treated with tantalum-containing compositions according to the values reported in the table. In FIG. 14, the zirconia specimens each were prepared from a 4Y-PSZ material and were treated with tantalum-containing compositions according to the values reported in the table. In FIG. 15, the zirconia specimens each were prepared from a 5Y-PSZ material and were treated with tantalum-containing compositions according to the values reported in the table.

The 3-point bending strength values of the samples treated with tanalum-containing compositions as shown in FIGS. 13-15 were highly dependent on the tantalum alkoxide concentration, but the organic additive (PVP) concentration did not significantly affect the mechanical strength of the specimens. The effect of improving the flexural strength and fracture toughness according to the methods and compositions described herein can be effectively applied even in the case of a zirconia materials containing 3 to 12 mol % of stabilizer.

As shown, the zirconia sintered bodies treated using the methods and compositions described herein exhibit improved fracture toughness and strength while maintaining desirable aesthetics, and can be used for high-quality dental prostheses having both aesthetic and mechanical properties. These materials can be used also in various engineering fields that require damage resistance.

We claim:

1. A method for enhancing the fracture toughness of an yttria-stabilized zirconia ceramic material comprising:
   a. applying a solution to a porous ceramic body that comprises an yttria-stabilized zirconia material stabilized by 3 mol % to 12 mol % yttria, the solution comprising
      1. 10 wt % to 80 wt % of a tantalum alkoxide;
      2. 20 wt % to 90 wt % of a co-solvent system comprising a first solvent and a second solvent that is different than the first solvent, and
      3. 0.1 wt % to 10 wt % of a soluble polymer that is soluble in a polar solvent;

b. penetrating at least a portion of the porous ceramic body with the solution; and c. drying and sintering the porous ceramic body.

2. The method of claim 1 wherein the tantalum alkoxide is present at a weight of 40 wt % to 80 wt %.

3. The method of claim 1 wherein the tantalum alkoxide is present at a weight of 40 wt % to 70 wt %.

4. The method of claim 1 wherein a sintered ceramic body made by the method comprises
  a. 4.5 to 6.5 mol % yttria,
  b. the solution comprises between 55 wt % and 60 wt % tantalum alkoxide, and
wherein the sintered ceramic body comprises a fracture toughness of >5 MPa·m$^{1/2}$.

5. The method of claim 1 wherein a sintered ceramic body made by the method comprises
  a. 4.5 to 5.2 mol % yttria,
  b. the solution comprises between 55 wt % and 60 wt % tantalum alkoxide, and
wherein the sintered ceramic body comprises a fracture toughness of >8 MPa·m$^{1/2}$.

6. The method of claim 1 wherein a sintered ceramic body made by the method comprises
  a. 5.3 to 5.8 mol % yttria,
  b. the solution comprises between 50 wt % and 60 wt % tantalum alkoxide, and
wherein the sintered ceramic body comprises a fracture toughness of >6 MPa·m$^{1/2}$.

7. The method of claim 1 wherein a sintered ceramic body made by the method comprises
  a. 4.5 mol % to 5.8 mol % yttria, and
  b. the solution comprises between 40 wt % and 65 wt % tantalum alkoxide, and
wherein the sintered ceramic body comprises a fracture toughness of >4 MPa·m$^{1/2}$.

8. The method of claim 7, wherein the solution comprises between 50 wt % and 65 wt % tantalum ethoxide, and wherein the sintered ceramic body comprises a fracture toughness of >5 MPa·m$^{1/2}$.

9. The method of claim 7 wherein the fracture toughness is >5 MPa·m$^{1/2}$ for a depth of at least 50 um.

10. The method of claim 7 wherein the fracture toughness is >5 MPa·m$^{1/2}$ for a depth of at least 100 um.

11. The method of claim 7 wherein the fracture toughness is >5 MPa·m$^{1/2}$ for a depth of at least 200 um.

12. The method of claim 1, wherein the porous ceramic body is in the shape of a restoration crown, and the solution is applied to a gingival margin region of the crown.

13. The method of claim 12, wherein the porous ceramic body upon sintering is a restoration crown that has a fracture toughness greater than 7 MPa·m$^{1/2}$ at the margin region, and a fracture toughness less than 5 MPa·m$^{1/2}$ at a distance of 1 mm from the margin region.

14. The method of claim 1, wherein a sintered ceramic body made by the method comprises a selective diffusion protective coating layer having a thickness of from about 50 μm to about 1500 μm and a depth of from about 0 μm to about 1000 μm from a surface of the sintered ceramic body to which the solution was applied.

15. The method of claim 1, wherein a sintered ceramic body made by the method comprises a selective diffusion protective coating layer having a thickness of from about 50 μm to about 300 μm and a depth of from about 50 μm to about 200 μm from a surface of the sintered ceramic body to which the solution was applied.

16. The method of claim 1, wherein a sintered ceramic body made by the method comprises a selective diffusion protective coating layer having a thickness of from about 50 μm to about 150 μm and a depth of from about 50 μm to about 200 μm from a surface of the sintered ceramic body to which the solution was applied.

17. The method of claim 1, wherein a sintered ceramic body made by the method comprises a selective diffusion protective coating layer having a thickness of from about 50 μm to about 300 μm and a depth of from about 0 μm to about 1000 μm from a surface of the sintered ceramic body to which the solution was applied.

18. The method of claim 1, wherein a sintered ceramic body made by the method comprises a selective diffusion protective coating layer having a thickness of from about 50 μm to about 150 μm and a depth of from about 0 μm to about 1000 μm from a surface of the sintered ceramic body to which the solution was applied.

* * * * *